US009618426B2

(12) United States Patent
Desai

(10) Patent No.: US 9,618,426 B2
(45) Date of Patent: Apr. 11, 2017

(54) TRANSPORTABLE QUANTITATIVE SAMPLE TRANSFER DEVICE

(76) Inventor: Manishkumar Desai, Shelby Township, MI (US)

(*) Notice: Subject to any disclaimer, the term of this patent is extended or adjusted under 35 U.S.C. 154(b) by 569 days.

(21) Appl. No.: 13/613,346

(22) Filed: Sep. 13, 2012

(65) Prior Publication Data

US 2013/0239707 A1    Sep. 19, 2013

Related U.S. Application Data

(63) Continuation-in-part of application No. 13/456,389, filed on Apr. 26, 2012.

(60) Provisional application No. 61/498,671, filed on Jun. 20, 2011.

(51) Int. Cl.
*G01N 1/00* (2006.01)
*B01L 3/02* (2006.01)
*G01N 35/00* (2006.01)

(52) U.S. Cl.
CPC ............. *G01N 1/00* (2013.01); *B01L 3/0289* (2013.01); *B01L 2200/141* (2013.01); *B01L 2300/041* (2013.01); *G01N 2035/00217* (2013.01)

(58) Field of Classification Search
None
See application file for complete search history.

(56) References Cited

U.S. PATENT DOCUMENTS

| 2,135,410 | A | * | 11/1938 | Ottoson | 222/129 |
| 2,601,039 | A | * | 6/1952 | Livingstone | 222/109 |
| 3,517,604 | A | * | 6/1970 | Coors | 99/323 |
| 5,734,006 | A | * | 3/1998 | Narayanan | A01N 25/34 424/470 |
| 6,431,417 | B1 | * | 8/2002 | Kumar | 222/571 |

OTHER PUBLICATIONS

2010-L87996, Jan. 2001, Guo.*

* cited by examiner

*Primary Examiner* — Robert R Raevis
(74) *Attorney, Agent, or Firm* — David P. Lhota, Esq; Lhota & Associates, P.A.

(57) ABSTRACT

A quantitative sample transfer device for receiving and holding a sample while it is weighed and for transferring the weighed sample material into a flask without losing any sample, the quantitative sample transfer device having a hollow central body segment with a flat bottom surface, a first hollow neck at one end of the central body, a second hollow neck at the opposite end of the central body, a removable first cap for occluding the first hollow neck, a removable second cap for occluding the second hollow neck, an opening in the central body for introducing a sample into the body, a lid permanently attachable to the body segment over the opening that remains permanently closed once closed and a set of lateral ridges on at least one neck that allow for the release of air when a solvent is introduced into the transfer device to flush any remaining sample into the container. The lid may be hinged to the body segment.

20 Claims, 19 Drawing Sheets

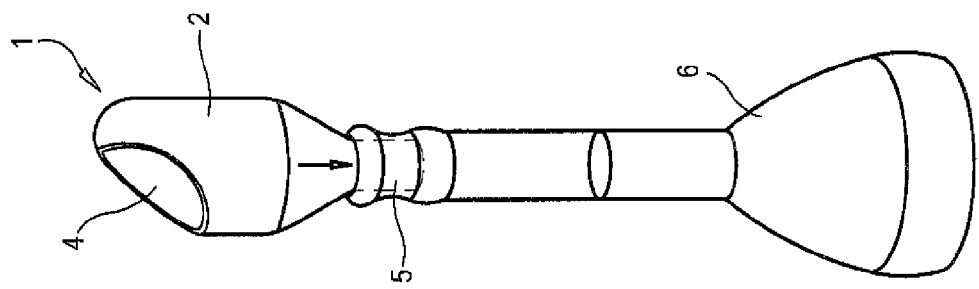
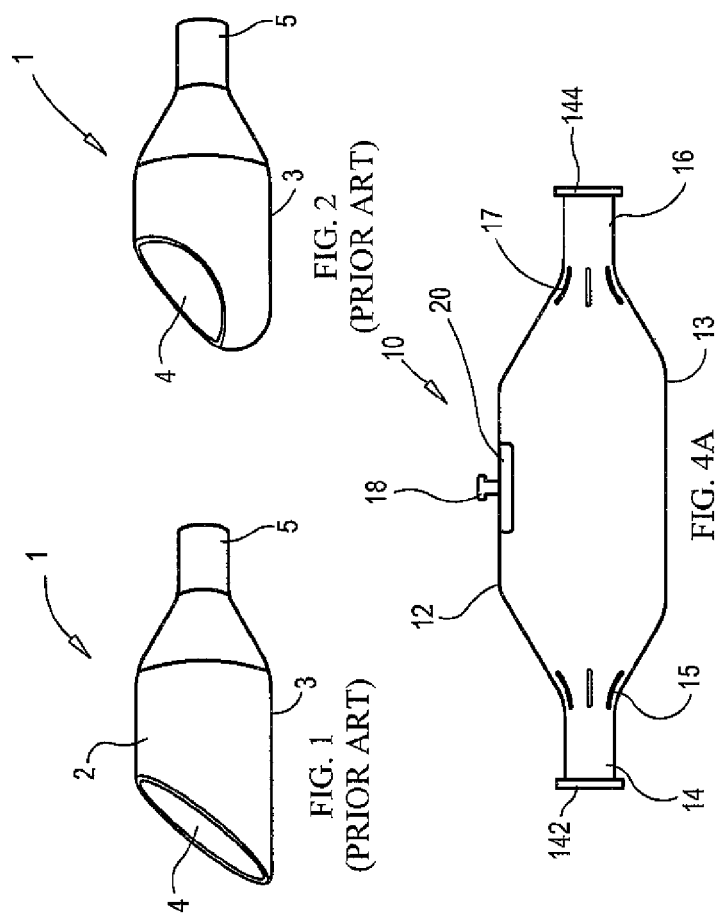
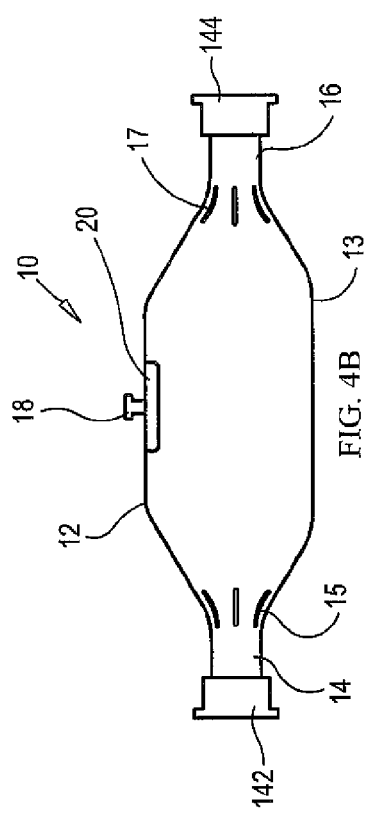

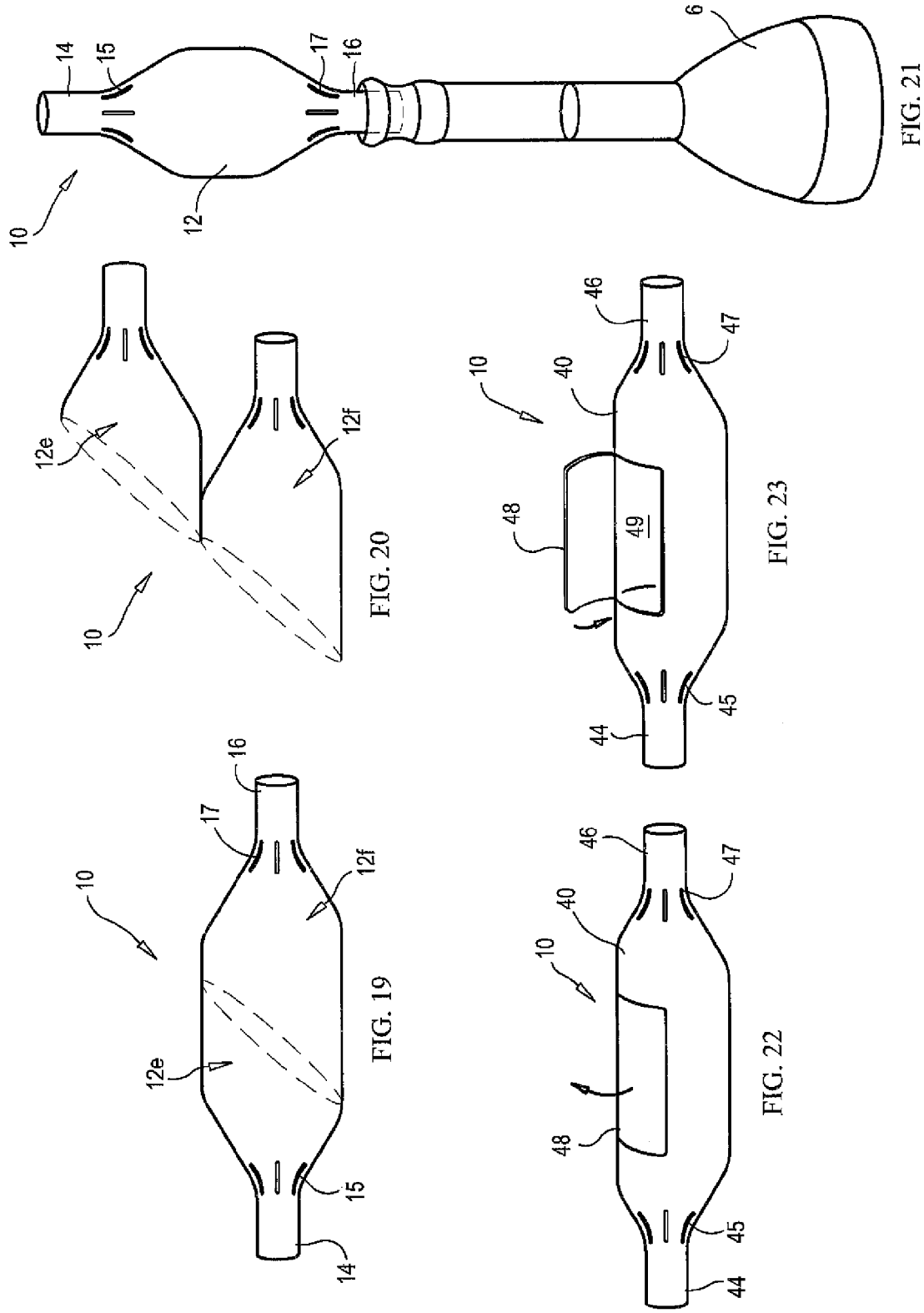

TRANSPORTABLE QUANTITATIVE SAMPLE TRANSFER DEVICE

CROSS REFERENCE TO RELATED APPLICATIONS

This application is a continuation-in-part of application Ser. No. 13/456,389 filed Apr. 26, 2012, which claims the benefit of provisional patent application Ser. No. 61/498,671 filed Jun. 20, 2011.

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyrights rights whatsoever.

BACKGROUND OF THE INVENTION

1. Field of the Invention

This invention relates generally to a weighing funnel that holds a chemical, pharmaceutical, biological or environmental sample (referenced herein as "sample") for transfer to a container, and more particularly, to a quantitative sample transfer device having a closed or closeable main body segment with a neck opening at each end and removable caps for plugging both neck ends, whereby at least one neck is insertable into a flask or container for transferring a chemical sample, and neck ridges for providing air release when a sample is transferred and rinsed into a flask so that none of the sample is lost during the transfer process.

2. Description of the Background Art

Weighing funnels for receiving a sample to be weighed are well known in the art and come in many sizes, ranging from 1 milliliter (ml) or less to 6 liters. With reference to the prior art drawings in FIGS. 1-3, known weighing funnels 1, such as those disclosed by Schneider in U.S. Pat. No. 6,179,022 and Des. 415,662, have a hollow and substantially cylindrical main body segment 2 with a flat bottom surface 3, a sample receiving opening 4 at one end and a pouring neck opening 5 at the opposite end. To weigh a sample, the flat bottom surface 3 of the weighing funnel 1 is placed on a weighing balance and then the sample is placed in the weighing funnel 1 through the sample receiving opening 4. Once weighed, the sample is transferred to a flask 6, or other desired container such as a volumetric flask or chemical flask 6, for testing by carefully orienting the pouring neck 5 downward and into the top of the flask 6 or other container while trying not to spill any weighed sample. Weighed sample remaining in the weighing funnel for along its sides, is rinsed into the flask by a solvent, such as methanol, saline or other desired solvent using a squirt bottle or dropper. Another method used to remove remaining weighed sample is by tapping the funnel or flask without the use of a solvent. It is very important not to lose any weighed sample to avoid having to repeat the entire process.

There are several problems with conventional weighing funnels of this variety, which all center on losing samples or material once they have been weighed resulting in erroneous analysis results, repeated tests, investigation costs and additional costs in material and labor. For instance, weighed samples are often spilled when moving the funnel to a flask 6. Another way in which weighed sample is lost is due to static, air currents, gravity or similar forces. Weighed samples are also lost when using a rinsing solvent with conventional weighing funnels, because the funnels are not closed or closeable and solvent splashes out compromising the integrity of the rinsing process and weighed sample. Another reason weighed material is lost during rinsing is because the weighing funnel makes an airtight fit in the flask or container leaving no way for air to escape as it is displaced with the sample and rinsing solvent. This keeps the air in the container from escaping during the transfer process which creates bubbles and back flow resulting in an inefficient, unreliable and erroneous transfer of material. Finally, attempting to remove remaining sample in the funnel by tapping the funnel or container invariably results in a loss of weighed material. The resulting additional costs in performing repeatedly these sample weighing and transfer procedures could be avoided if there existed a closed or closeable quantitative sample transfer device, however, there are no known funnels that adequately and effectively address these issues.

Various other funnel devices are known in the background art but they also fail to address or even contemplate the aforementioned shortcomings. For instance, U.S. Pat. Nos. 6,173,603 and 5,918,273 issued to Horn, discloses a funnel and one-piece column arrangement for retaining small quantities of chemical samples. U.S. Pat. No. 7,461,542, issued to Weisinger, discloses a funnel viscosimeter wherein a Marsh funnel is equipped with a valve at the funnel outlet. U.S. Pat. No. 5,277,234, issued to Warstler, discloses a self venting funnel having a plurality of spaced parallel channels and a spring housing and spring loaded button. U.S. Pat. No. 4,068,689, issued to Krull, discloses a funnel securable to the uncovered top of a receptacle containing dry pulverized material is provided with an encircling skirt which coacts with the funnel to define a relatively closed zone encompassing the discharge mouth of the funnel. U.S. Pat. No. 7,225,689 and U.S. Patent Application Pub. No. 2005/0142031, issued to Wickstead et al., disclose a funnel collector that collects and holds a fluid sample in order to place the sample in immediate contact with a diagnostic test strip, which reacts with the sample. U.S. Pat. No. 3,807,466, issued to Minneman, discloses a loading funnel for ammunition cases that includes a variety of interchangeable adapter tubes, each adapted to a particular size of cartridge to prevent choking or bridging of the powder for free flow directly into the cartridge. Lastly, U.S. Patent Application Pub. No. 2007/0034421, issued to Ho et al., discloses a weighing spoon having a spoon body, holder body and a level meter. The foregoing patents and published patent applications disclose devices unrelated to the problems with conventional weighing funnels, are used for entirely different purposes and comprise structure that does not address and cannot resolve the aforementioned issues.

As there are no known quantitative sample transfer devices that address the issues noted herein, there exists a need for such a device. It is, therefore, to the effective resolution of the aforementioned problems and shortcomings of the prior art that the present invention is directed. The instant invention addresses this unfulfilled need in the prior art by providing a quantitative sample transfer device as contemplated by the instant invention disclosed herein.

OBJECTS OF THE INVENTION

In light of the foregoing, it is an object of the present invention to provide a quantitative sample transfer device that prevents the loss of sample or material when moving the transfer device to a new location or flask or during the transfer process into a flask or other container.

It is also an object of the instant invention to provide a quantitative sample transfer device that prevents the loss of sample or material due to static during the transfer process into a flask or other container.

It is another object of the instant invention to provide a quantitative sample transfer device that prevents the loss of sample or material due to splashing during the transfer process into a flask or other container.

It is an additional object of the instant invention to provide a quantitative sample transfer device that prevents the loss of sample or material due to back flow caused by displaced and trapped air during the transfer process into a flask or other container.

It is a further object of the instant invention to provide a quantitative sample transfer device that saves costs due to loss sample or material during the transfer process.

It is yet another object of the instant invention to provide a quantitative sample transfer device that avoids material and labor costs due to repeating the measurement and transfer process when sample or material is lost.

It is yet a further object of the instant invention to provide a quantitative sample transfer device that quantitatively transfers a sample to any container for further analysis and weighing.

It is yet an additional object of the instant invention to provide a quantitative sample transfer device that facilitates accurate test results.

It is yet another object of the instant invention to provide a quantitative sample transfer device that facilitates improved quality control.

It is yet a further object of the instant invention to provide a quantitative sample transfer device that is amenable to mass production.

It is still another object of the instant invention to provide a quantitative sample transfer device that is disposable.

It is still an additional object of the instant invention to provide a quantitative sample transfer device that is made of glass so it is reusable.

It is still a further object of the instant invention to provide a quantitative sample transfer device that is cost effective.

In light of these and other objects, the instant invention provides a quantitative sample transfer device (generally referenced herein as a "transfer device") for receiving and holding a sample while it is weighed and for transferring the weighed sample material into a flask, volumetric flask, chemical flask or other container (generally referenced herein as "flask") without losing any sample. The quantitative sample transfer device preferably comprises a hollow central body segment with a flat bottom surface, a first neck at one end of the central body, a second neck at the opposite end of the central body, an opening in the central body for introducing a sample into the body, a lid over the opening that remains permanently closed once closed, a pair of removable caps for plugging each end of the transfer device during transit and a set of lateral ridges on each neck that allow for the release of air when a solvent is introduced into the transfer device to flush any remaining sample into the container. The transfer device may also include a small handle protruding from the top surface of the lid for lifting the device. In the first and most basic embodiment, a chemical sample material is introduced into the central body through the central body opening while the transfer device rests on the flat bottom surface on a scale. Once the sample is introduced into the transfer device and weighed, the transfer device lid is closed and snapped shut. Thereafter, a cap is mounted to each neck to prevent spilling the sample when transporting the device to a flask or other location. The device is next moved to a flask with the caps plugging each neck end to avoid spillage, at least one cap is removed when reaching the flask, and the device is then tilted over the container while one neck is placed into the flask opening causing the sample to pour into the flask. A solvent, such as methanol, saline or other desired solvent, is introduced into the transfer device by squirting or dropping it through the opposite neck to rinse any remaining sample into the flask. When rinsing, any air displaced exits through the channels formed between the ridges, the inserted neck and flask opening.

The quantitative sample transfer device also comprises a number of other embodiments having lids that are opened to introduce a sample into the transfer device and that are closed to prevent any sample spillage, as disclosed in the U.S. parent patent application Ser. No. 13/456,389, filed Apr. 26, 2012, which is incorporated herein by reference. One embodiment comprises a transverse lid hinged to the top surface of the transverse device over a corresponding opening perpendicular to the longitudinal axis of the transfer device. A second embodiment comprises a lateral lid hinged to the top surface of the transverse device over a corresponding opening in line with the longitudinal axis of the transfer device. In both embodiments, the lid is swung open to introduce a sample and closed and snapped shut to close the opening and prevent loss of sample during movement. Either neck may be placed in the container for the transfer process with the other neck being used for rinsing with a solvent. These embodiments may be altered by making one neck end with a flared construction to provide a wider opening for rinsing. These embodiments may also be altered with a flat top surface and with lids and the bottom half of the transfer device with a flat bottom surface and, or tapered sides.

In other alternative embodiments, the quantitative sample transfer device has a two-piece central body segment. In one of these embodiments, the two central body segments have an angled cooperating cross section and are snapped together to form an airtight seal. In another embodiment, the two central body segments have an angled cooperating cross section that are hinged together such that one segment swings on top of the other central body segment to introduce a sample in the lower segment and is swung back down and snapped shut against the other piece segment to form an airtight seal. In another embodiment, the quantitative sample transfer device comprises an upper segment and lower segment. The upper segment has an opening with a hinged lid for accessing and closing the opening and a lower segment. The upper segment is preferably truncated with tapered sides and a flat top surface. The lower segment is preferably truncated with tapered sides and a flat bottom surface. The upper and lower segments snap together to form an airtight seal.

In accordance with these and other objects, which will become apparent hereinafter, the instant invention will now be described with particular reference to the accompanying drawings.

BRIEF DESCRIPTION OF THE SEVERAL VIEWS OF THE DRAWINGS

FIG. 1 is a perspective view of a prior art weighing funnel.

FIG. 2 is a perspective view of another prior art weighing funnel.

FIG. 3 is a perspective view of a prior art weighing funnel mounted in a flask.

FIG. 4a is an elevational view of the quantitative sample transfer device with caps plugging the neck ends in accordance with a third embodiment of the instant invention.

FIG. 4b is an elevational view of the quantitative sample transfer device with caps mounted over and blocking the neck ends in accordance with a fourth embodiment of the instant invention.

FIG. 19 is a perspective view of the quantitative sample transfer device having a two segment body with an angled hinged connection showing the segments connected in accordance with a ninth embodiment of the instant invention.

FIG. 20 is a perspective view of the quantitative sample transfer device having a two segment body with an angled hinged connection showing the segments open in accordance with the ninth embodiment of the instant invention.

FIG. 21 is a perspective view of the quantitative sample transfer device showing one of the cylindrical embodiments mounted in a flask container in accordance with the instant invention.

FIG. 22 is a perspective view of the quantitative sample transfer device with an elongated central body segment, lid and top opening showing the lid closed in accordance with a tenth embodiment of the instant invention.

FIG. 23 is a perspective view of the quantitative sample transfer device with an elongated central body segment, lid and top opening showing the lid opened in accordance with the tenth embodiment of the instant invention.

DETAILED DESCRIPTION OF THE INVENTION

Figure 5:
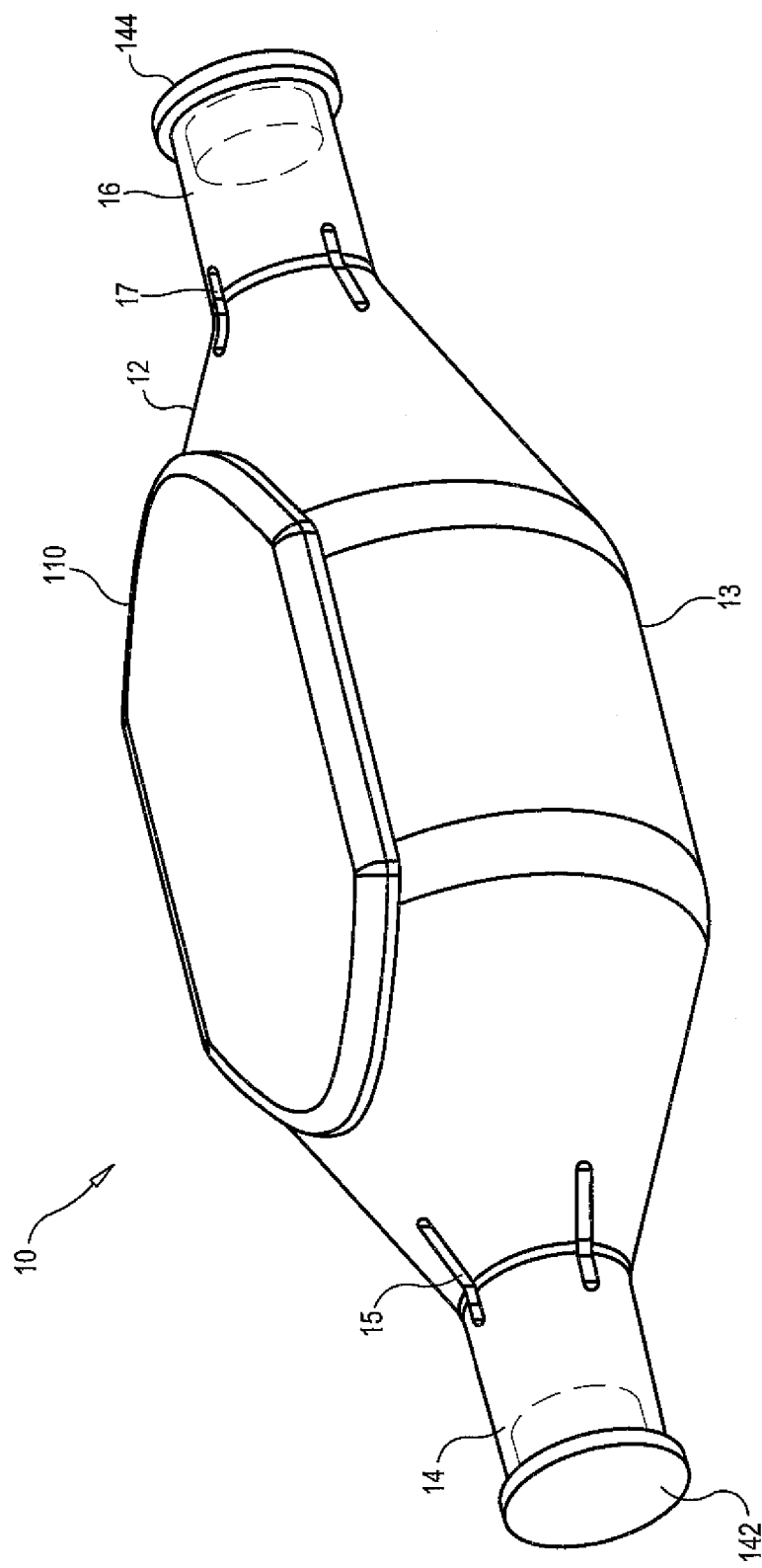
FIG. 5 is a perspective view of the quantitative sample transfer device with a lid covering the top opening showing the lid snapped closed and the end caps plugged into the neck ends in accordance with the preferred embodiment of the instant invention.
Figure 6:
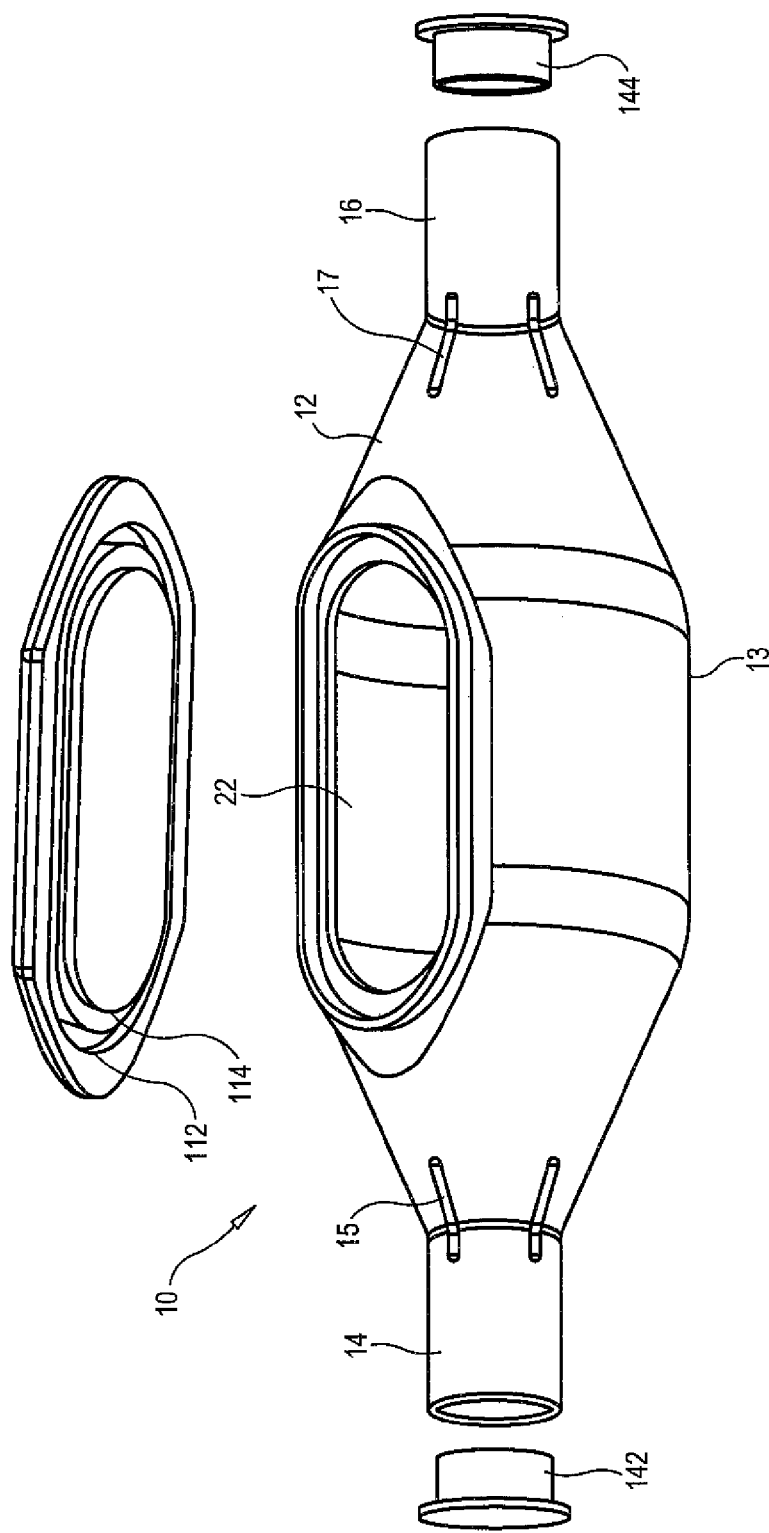
FIG. 6 is an exploded perspective view of the quantitative sample transfer device with a lid over the top opening showing the lid open and the caps prior to plugging into the neck ends in accordance with the preferred embodiment of the instant invention.
Figure 7:
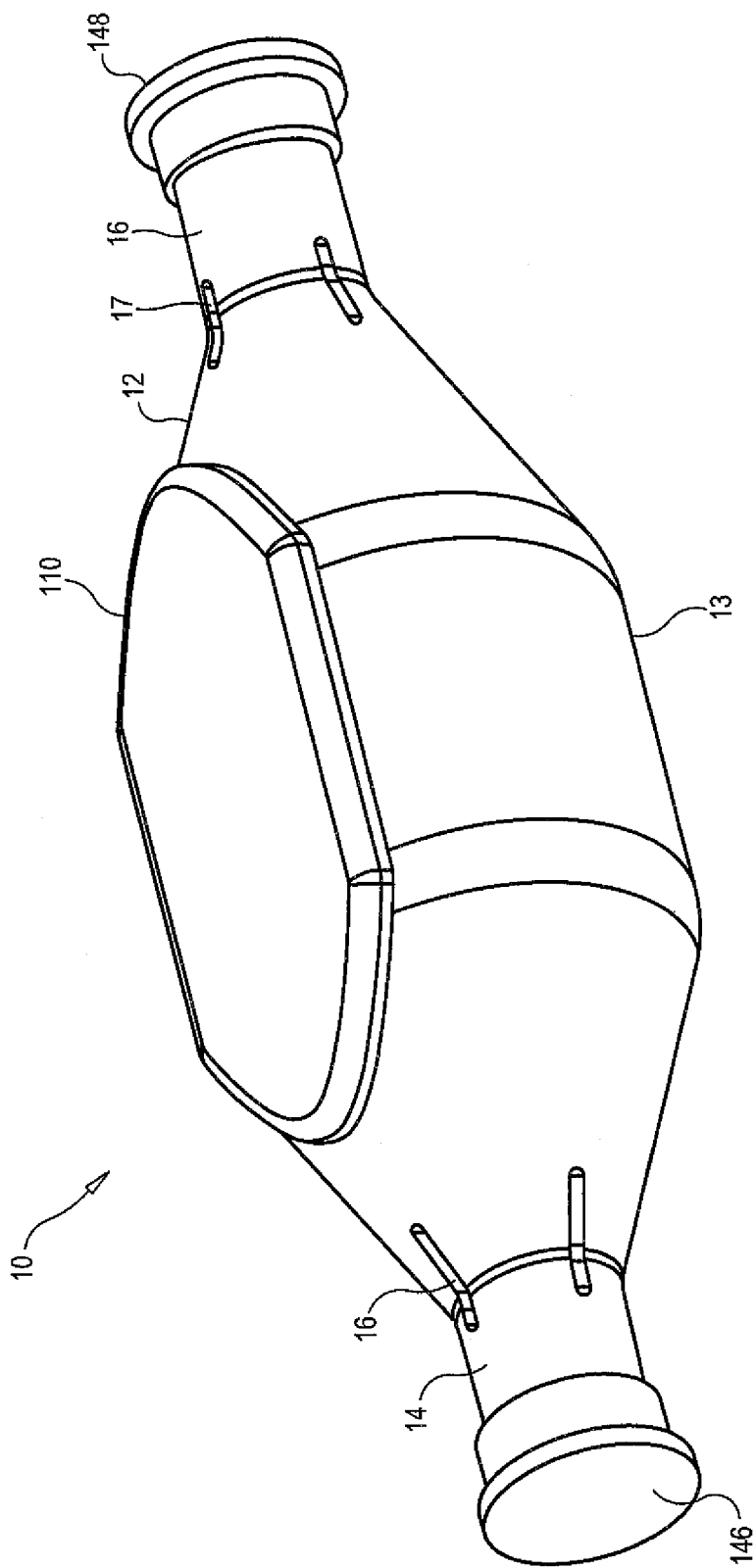
FIG. 7 is a perspective view of the quantitative sample transfer device with a lid over the top opening showing the lid snapped closed and the plugs mounted over and blocking the neck ends in accordance with an alternative embodiment of the instant invention.
Figure 8:
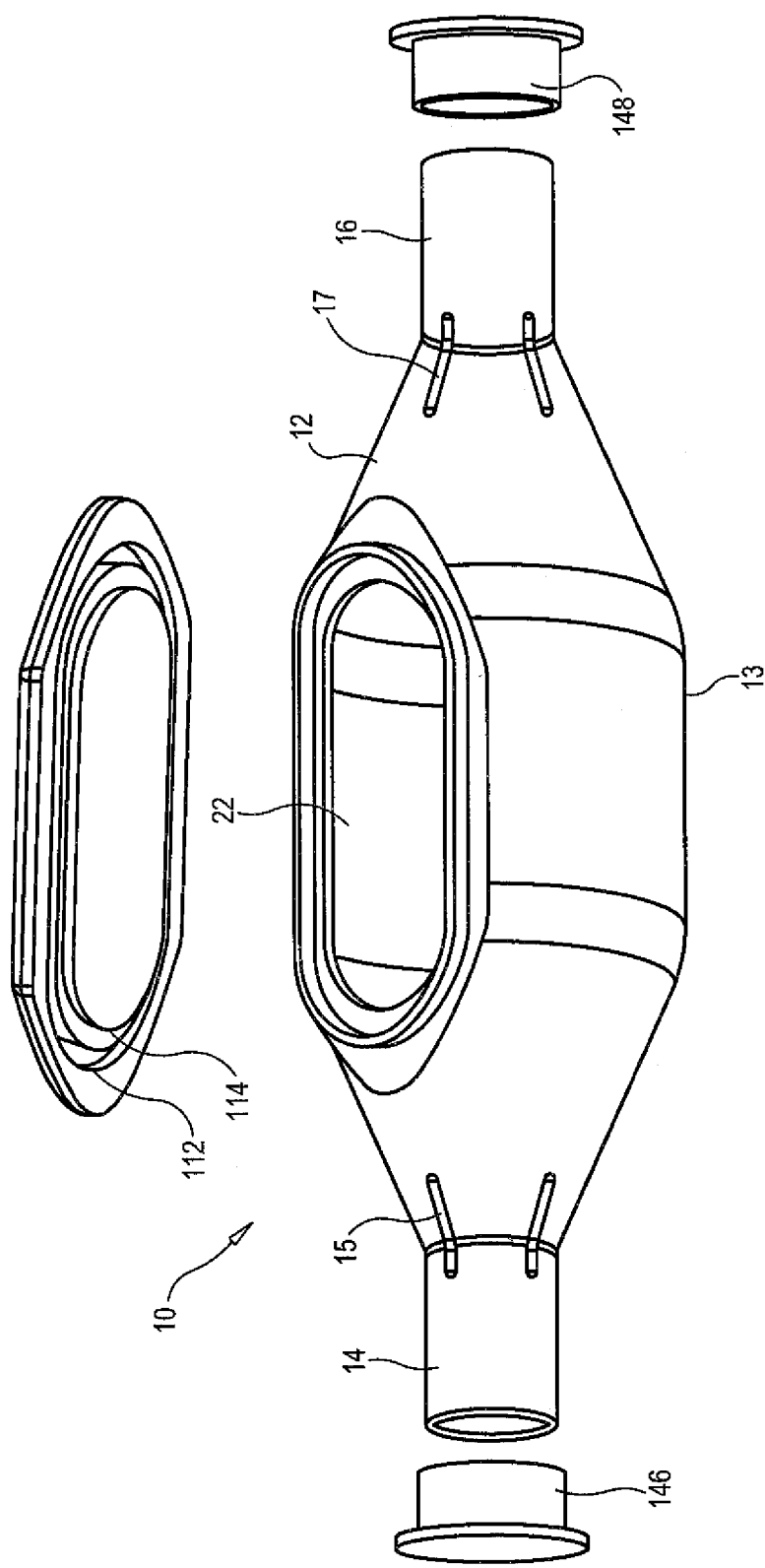
FIG. 8 is a perspective view of the quantitative sample transfer device with a lid over the top opening showing the lid open and the plugs prior to mounting over and blocking the neck ends in accordance with the alternative embodiment of the instant invention.

With reference to the drawings, FIGS. 4a-41 depict the preferred and alternative embodiments of the instant invention which is generally referenced as a quantitative sample transfer device, sample transfer device, transfer device and, or by numeric character 10. The quantitative sample transfer device 10 comprises a tool for receiving and holding a sample without the risk of spilling it while the sample is weighed and moved to another location and for transferring the weighed sample material into a flask, volumetric flask, chemical flask or other container (generally referenced herein as "container") without losing any sample. The quantitative sample transfer device 10 comprises a closed or closable funnel with removable neck end caps 142, 144 that prevents the loss of sample or material due to splashing, back flow or static during the transfer and rinsing process. The transfer device 10 quantitatively transfers a sample to any container for weighing and analysis without the risk of losing any of the sample thereby facilitating accurate test results. The ability to weigh a sample and transfer it without the risk of loss facilitates accurate testing, prevents the waste of sample and time and having to repeat measurements, weighing and tests while improving quality control of test results.

With reference to FIGS. 5-10, the preferred and alternative embodiments of the quantitative sample transfer device 10 generally comprises a hollow central body segment 12 with a flat bottom surface 13, a first neck 14 at one end of the central body 12, a second neck 16 at the opposite end of the central body 12, an opening 22 in the central body 12 for introducing a sample into the body 12, a lid 20/30 or a lid 110 over the opening 22 that remains permanently closed once closed, a first removable cap 142 that plugs into or mounts over the first neck 14, a second cap 144 that plugs into or mounts over the second neck 16, and a set of lateral ridges 15, 17 on each neck 14, 16 that allow for the release of air when a solvent is introduced into the transfer device 10 to flush any remaining sample into a container. The caps 142, 144 may be used with all embodiments of the transfer device 10 shown in FIGS. 4A-41. With reference to FIGS. 4A-4B, the third and fourth embodiments of the transfer device 10 includes a small handle 18 protruding from the top surface of the lid 20/30 for lifting the device 10 once the lid 20/30 is closed, as shown in FIGS. 4A-4B. With reference to FIGS. 5-10, the transfer device 10 comprises a lid 110 that snaps permanently to the central body 12. The lid 110 may be snapped onto the central body 12 using any of the snapping structures shown in FIGS. 32-41. Referring to FIGS. 4A-10, a sample material is introduced into the central body 12 through the central body opening 22 while the transfer device 10 rests on its flat bottom surface 13 on a scale. Once the sample is introduced into the transfer device 10 and weighed, the lid 20/30 or 110 is closed permanently, the caps 142, 144 are plugged into or mounted over the first neck 14 and second neck 16, respectively, and the device 10 is moved to a container 6 wherein the caps 142 and 144 prevent spillage from the neck ends 14, 16. Thereafter, at least one cap 142 or 146 is removed and the device 10 is tilted over the container 6 while one neck 14 or 16 is placed into the container opening causing the sample to pour into the container 6. As some sample material often remains in the transfer device 10, a solvent, such as methanol, saline or other desired solvent, is squirted or dripped into the transfer device through the exposed or opposite neck 16 or 14 to rinse any remaining sample into the container. When rinsing, any air displaced exits through the channels formed between the ridges 15 or 17, the inserted neck 14 or 16 and interior walls of the container opening.

Various lids may be employed by the quantitative sample transfer device 10. All the lids disclosed herein are for use with the disposable versions of the sample transfer device 10 and preferably remain permanently closed once closed. The lids may comprise separate components from the body segment or may be hinged to the body segment. The lids and central body segment openings disclosed herein may incorporate any of the snapping configurations shown in FIGS. 32-41. The openings may also have a slightly recessed lip for facilitating a flush fit with the central body segments when the lids are closed.

Figure 10:
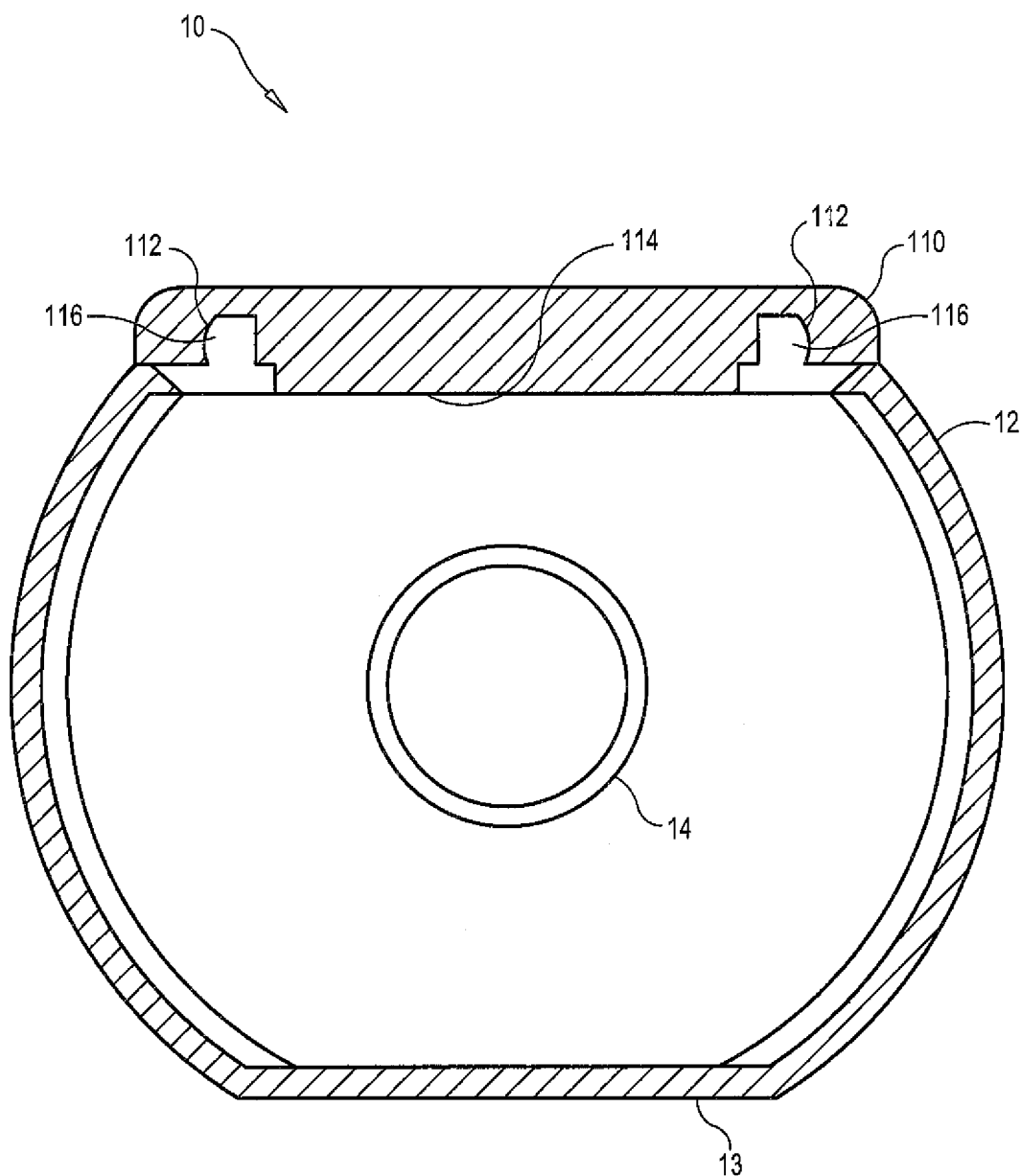
FIG. 10 is a cross sectional view of the quantitative sample transfer device and lid snapped and attached to the body segment showing the preferred structure for snapping the lid to the body segment in accordance with the instant invention.
Figure 11:
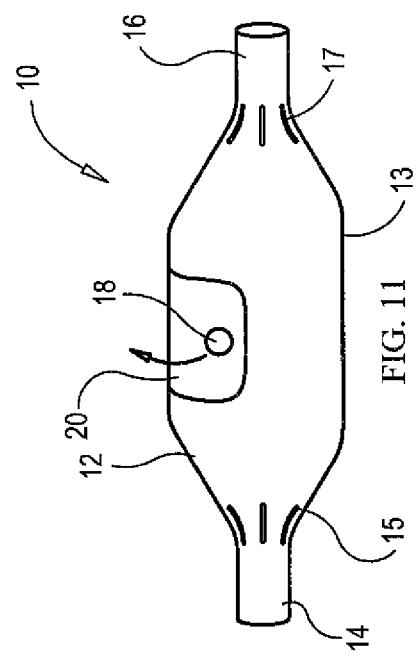
FIG. 11 is a perspective view of the quantitative sample transfer device with a lid over the top opening showing the lid closed in accordance with a fifth embodiment of the instant invention.
Figure 12:
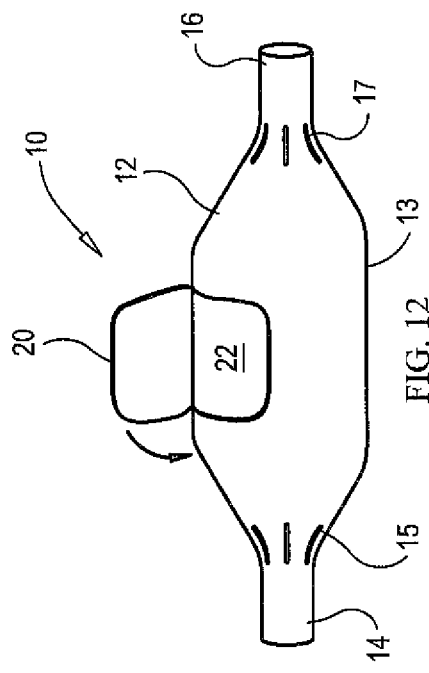
FIG. 12 is a perspective view of the quantitative sample transfer device with a lid over the top opening showing the lid open in accordance with the fifth embodiment of the instant invention.
Figure 13:
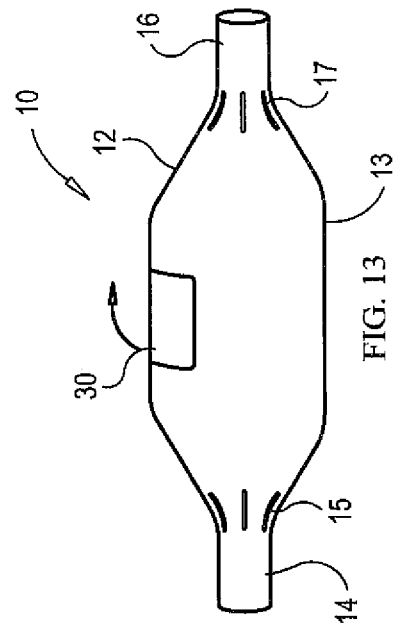
FIG. 13 is a perspective view of the quantitative sample transfer device with a lid over the top opening showing the lid closed in accordance with a sixth embodiment of the instant invention.
Figure 14:
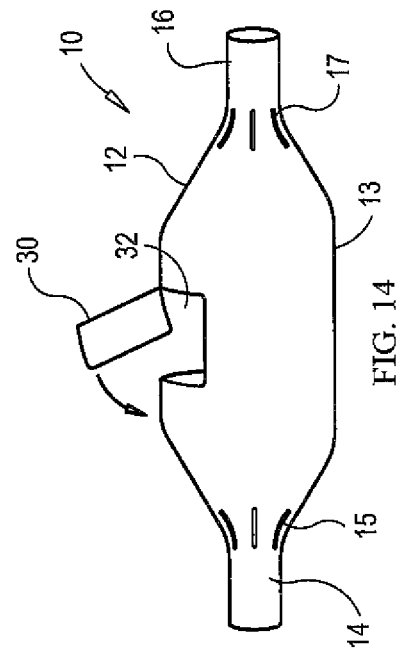
FIG. 14 is a perspective view of the quantitative sample transfer device with a lid over the top opening showing the lid open in accordance with the sixth embodiment of the instant invention.

Referring to FIGS. 11 and 12, in the fifth embodiment of the quantitative sample transfer device 10 comprises a transverse lid 20 hinged to the top surface of the central body segment 12 over a corresponding opening 22 perpendicular to the longitudinal axis of the transfer device central body 12. Referring to FIGS. 13 and 14, the sixth embodiment comprises a lateral lid 30 hinged to the top surface of the central body segment 12 over a corresponding opening 32 in line with the longitudinal axis of the transfer device central body 12. In both embodiments, the lid 20/30 is initially open to introduce a sample and closed and snapped shut permanently to close the opening and prevent loss of sample during movement. Either neck 14 or 16 may be placed in the container for transferring the sample into the container 6 with the other neck 16 or 14 being used for rinsing with a solvent to remove any remaining sample material, as shown in FIG. 21. The caps 142 and 144 may be used with these embodiments as well as all embodiments shown in FIGS. 4A-41.

Referring to FIGS. 22 and 23, the quantitative sample transfer device 10 may comprise an elongated construction for a wider opening. The elongated sample transfer device 40 comprises an elongated central body segment 40, a first neck 44 with a first set of ridges 45 projecting therefrom, a second neck 46 with a second set of ridges 47 projecting therefrom, a hinged door 48 and an access opening 49 to introduce sample into the central body 40, as well as caps 142 and 144.

Figure 15:
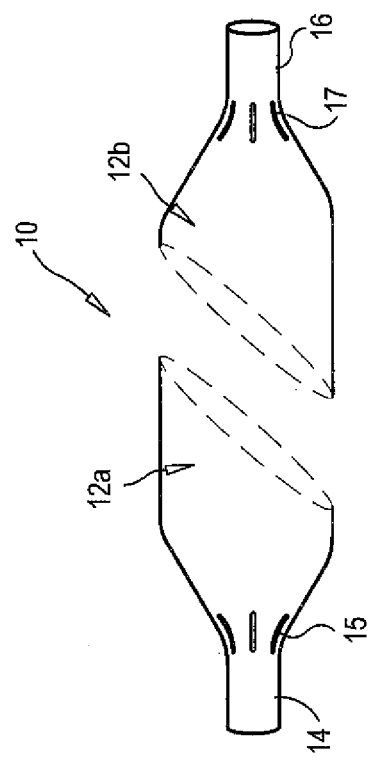
FIG. 15 is a perspective view of the quantitative sample transfer device having a two segment body with an angled connection showing the segments connected in accordance with a seventh embodiment of the instant invention.
Figure 16:
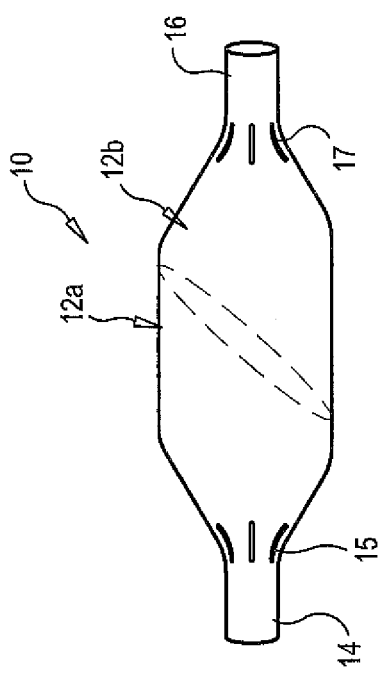
FIG. 16 is a perspective view of the quantitative sample transfer device having a two segment body with an angled connection showing sections separated in accordance with the seventh embodiment of the instant invention.
Figure 17:
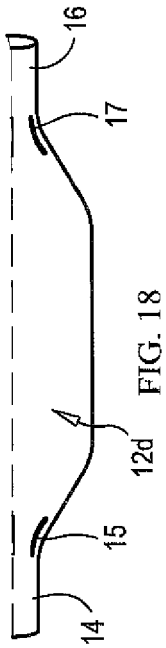
FIG. 17 is a perspective view of the quantitative sample transfer device having a two segment body with a top section and bottom section showing the top and bottom sections connected in accordance with an eighth embodiment of the instant invention.
Figure 18:
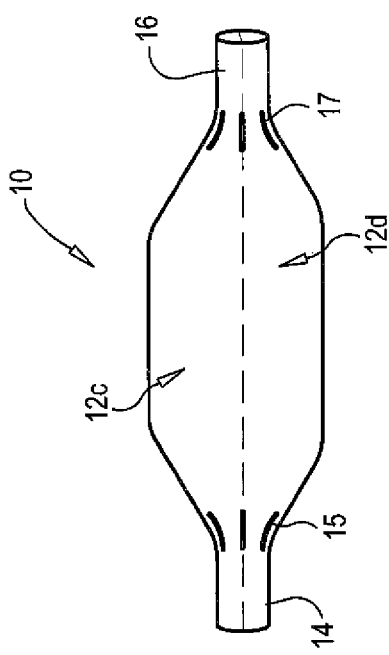
FIG. 18 is a perspective view of the quantitative sample transfer device having a two segment body with a top section and bottom section showing the top and bottom sections separated in accordance with the eighth embodiment of the instant invention.

Referring to FIGS. 15-20, in other alternative embodiments the quantitative sample transfer device 10 has a two-piece central body segment where the body segments are snapped together using one of the snapping structures shown in FIGS. 32-41 and includes caps 142 and 144. With reference to FIGS. 15 and 16, in accordance with the seventh embodiment of the transfer device 10, the central body 12 has two central body segments 12a, 12b with angled cooperating cross sections that are snapped together to form an airtight seal after a sample is introduced and includes caps 142 and 144. Once snapped together, the two body segments 12a, 12b are permanently snapped together. In the eighth embodiment, the central body 12 comprises an upper central body segment 12c and a lower central body segment 12d that snap together after a sample has been introduced, as shown in FIGS. 17 and 18. The upper segment 12c has an opening with a hinged lid for accessing and closing the opening. The upper segment 12c is preferably truncated with tapered sides and a flat top surface. The lower segment 12d is also truncated with tapered sides and a flat bottom surface. The upper and lower segments 12c, 12d are snapped together to form an airtight seal. With reference to FIGS. 19 and 20, in the ninth embodiment the central body 12 comprises a first body segment 12e and second body segment 12f having cooperating angled cross sections that are hinged together such that one segment 12e swings on top of the other central body segment 12f to introduce a sample in the lower segment 12e and is swung back down and snapped shut permanently against the lower piece segment 12f to form an airtight seal and comprises caps 142, 144. With reference to FIGS. 22 and 23, the tenth embodiment of the transfer device 10 comprises an elongated central body segment 40, a lid 48 that snaps shut over opening 49 and necks 14, 16 at each end that may be occluded by caps 142 and 144.

Figure 25:
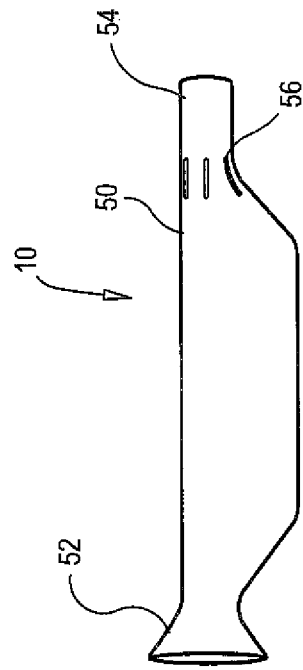
FIG. 25 is a perspective view of the quantitative sample transfer device having a flared solvent receiving neck end and a flat top surface in accordance with a twelfth embodiment of the instant invention.
Figure 27:
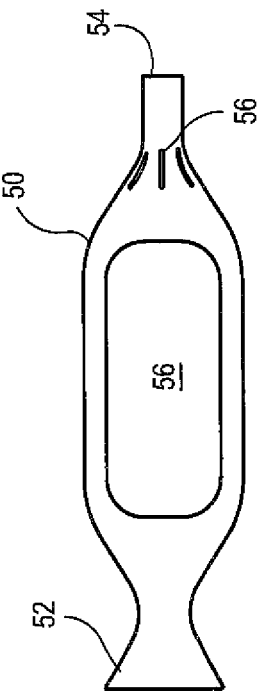
FIG. 27 is a perspective view of the quantitative sample transfer device having a flared solvent receiving neck end and an opening with a cover in accordance with the thirteenth embodiment of the instant invention.
Figure 29:
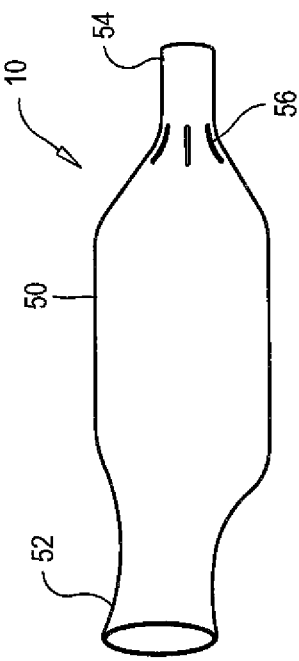
FIG. 29 is a perspective view of the quantitative sample transfer device having a flared and enlarged solvent receiving neck end and a flat top surface in accordance with a fifteenth embodiment of the instant invention.
Figure 24:
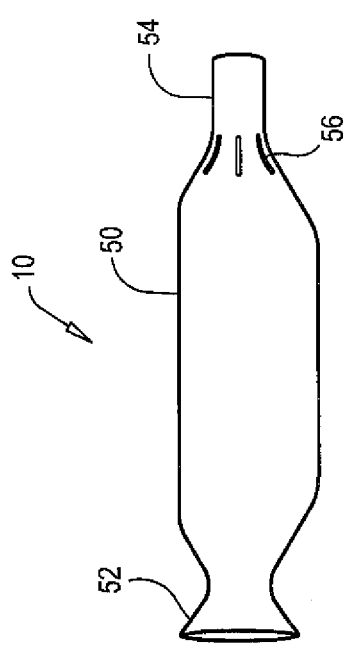
FIG. 24 is a perspective view of the quantitative sample transfer device having a flared solvent receiving neck end in accordance with an eleventh embodiment of the instant invention.
Figure 26:
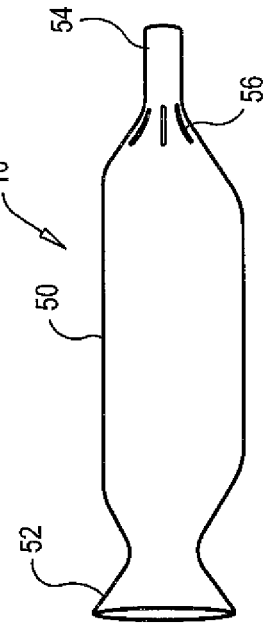
FIG. 26 is a perspective view of the quantitative sample transfer device having a flared solvent receiving neck end and an opening with a cover (not shown) on the opposite side in accordance with a thirteenth embodiment of the instant invention.
Figure 28:
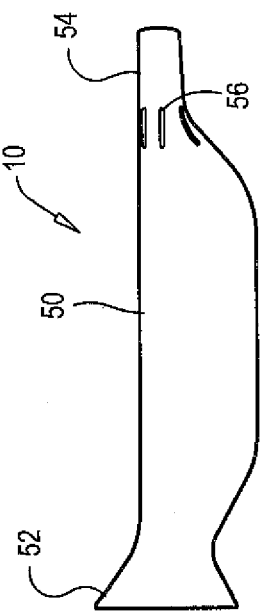
FIG. 28 is a perspective view of the quantitative sample transfer device having a larger flared solvent receiving neck end and a flat top surface in accordance with a fourteenth embodiment of the instant invention.
Figure 31:
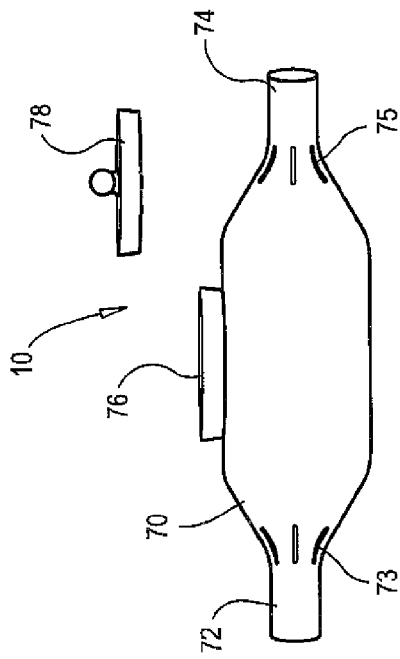
FIG. 31 is a perspective view of the quantitative sample transfer device having a glass body and lid in accordance with a seventeenth embodiment of the instant invention.
Figure 30:
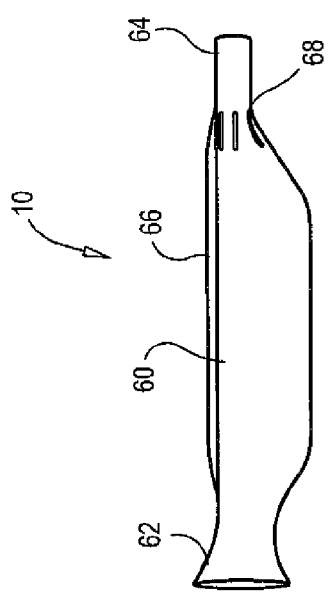
FIG. 30 is a perspective view of the quantitative sample transfer device having a flared solvent receiving neck end and a flat top surface and cover in accordance with a sixteenth embodiment of the instant invention.

With reference to FIGS. 24-29, these embodiments comprise a solvent receiving neck end with a flared construction to provide a wider opening for rinsing with solvent and caps 142, 144. With reference to FIGS. 24-25, in the eleventh and twelfth embodiments of the instant invention 10 the sample transfer device 10 comprises an elongated central body 50 with a flat top surface, a flared solvent receiving end 52 and a pouring neck 54 with a set of pressure relief ridges 56 and may include caps 142 and 144. With reference to FIGS. 26-27, in the thirteenth embodiment of the instant invention 10 the sample transfer device 50 comprises an elongated central body 50 with a slidable lid 56, a flared solvent receiving end 52 and a pouring neck 54 with a set of pressure relief ridges 56 and may also include caps 142, 144. With reference to FIGS. 28-29, in the fourteenth and fifteenth embodiments of the instant invention 10 the sample transfer device 10 comprises an elongated central body 50 with a flat top surface, a flared solvent receiving end 52 and a pouring neck 54 with a set of pressure relief ridges 56 and may include caps 142, 144. With reference to FIG. 30, in the sixteenth embodiment of the instant invention 10 the sample transfer device 60 comprises an elongated central body with a flat top surface 66, a flared solvent receiving end 62 and a pouring neck 64 with a set of pressure relief ridges 68 and may include caps 142, 144. With reference to FIG. 31, in the seventeenth embodiment the quantitative sample transfer device 70 comprises a glass central body with a first neck 72 and ridges 73, second neck 74 and ridges 75, an opening 76 with a raised lip and a glass lid 78 and may include caps 142, 144.

Referring to FIGS. 4a-30 and 32-41, the disposable versions of the quantitative sample transfer devices 10 are manufactured from a plastic material. The preferred plastic materials for construction of the disposable transfer devices 10 comprise polypropylene, acrylonitrile styrene (ABS), polyethylene, acrylic, hardened acrylic, high impact polystyrene, vinyl, nylon, polycarbonate or combinations thereof.

Referring to FIG. 31, the reusable version of the quantitative sample transfer device 10 is preferably made from a glass material to facilitate cleaning and sterilization. The preferred glass material for construction of the reusable sample transfer device 10 comprises glass or porcelain. In an alternative embodiment, the reusable sample transfer device 10 may be constructed from certain metals and alloys, such as stainless steel.

Figure 34:
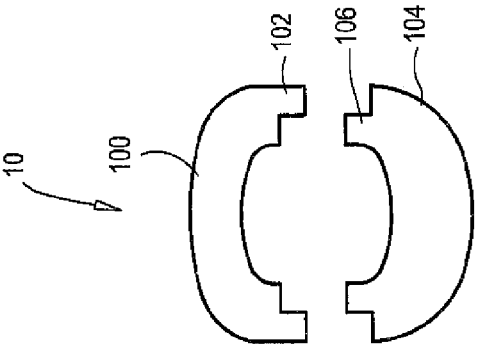
FIG. 34 is an elevational cross section view of a two piece quantitative sample transfer device showing a third structure for snapping the two pieces together in accordance with the instant invention. This snapping configuration may also be used to permanently close the lids in all embodiments.
Figure 33:
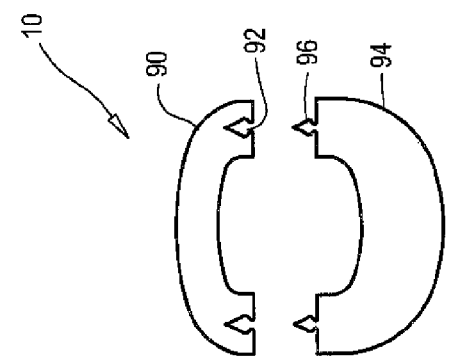
FIG. 33 is an elevational cross section view of a two piece quantitative sample transfer device showing a second structure for snapping the two pieces together in accordance with the instant invention. This snapping configuration may also be used to permanently close the lids in all embodiments.
Figure 32:
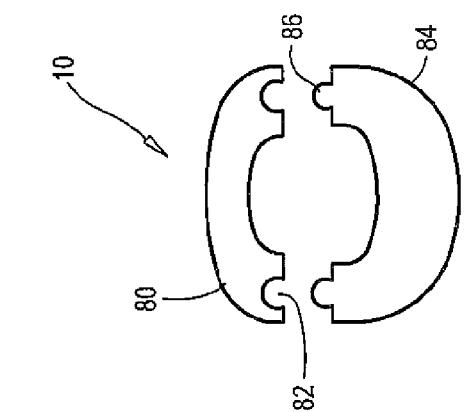
FIG. 32 is an elevational cross section view of a two piece quantitative sample transfer device showing a first structure for snapping the two pieces together in accordance with the instant invention. This snapping configuration may also be used to permanently close the lids in all embodiments.

With reference to FIGS. 32-41, the quantitative sample transfer device 10 preferably comprises a variety of lids and cooperating body attachment structure for snapping to the central body segment over its opening 22 to prevent the loss or spillage of sample when moving the transfer device 10 and pouring its contents into a flask. The various lid embodiments may be snapped to the central body segment as follows. With reference to FIG. 32, in a first embodiment for snapping the lid to the body segment, the transfer device 10 comprises a central body segment 84 having a curved rail 86 projecting upward from and around the periphery of the body segment 84 and a lid 80 having a corresponding curved groove 82 formed around the periphery of the lid's lower periphery surface. The rail 86 and groove 82 snap together when aligned and pressed shut. With reference to FIG. 33, in a second embodiment for snapping the lid to the body segment, the transfer device 10 comprises a central body segment 94 having a tapered rail 96 projecting upward from and around the periphery of the body segment 94 and a lid 90 having a corresponding tapered groove 92 formed around the periphery of the lid's lower periphery surface. The rail 96 and groove 92 snap together when aligned and pressed shut. With reference to FIG. 34, in a third embodiment for snapping the lid to the body segment, the transfer device 10 comprises a central body segment 104 having a recessed ledge 106 formed around the periphery of the upper surface of the body segment 104 and a lid 100 with a corresponding flange 102 depending around the periphery of the lid 100. The recessed ledge 106 and flange 102 snap together when aligned and pressed shut.

Figure 9:
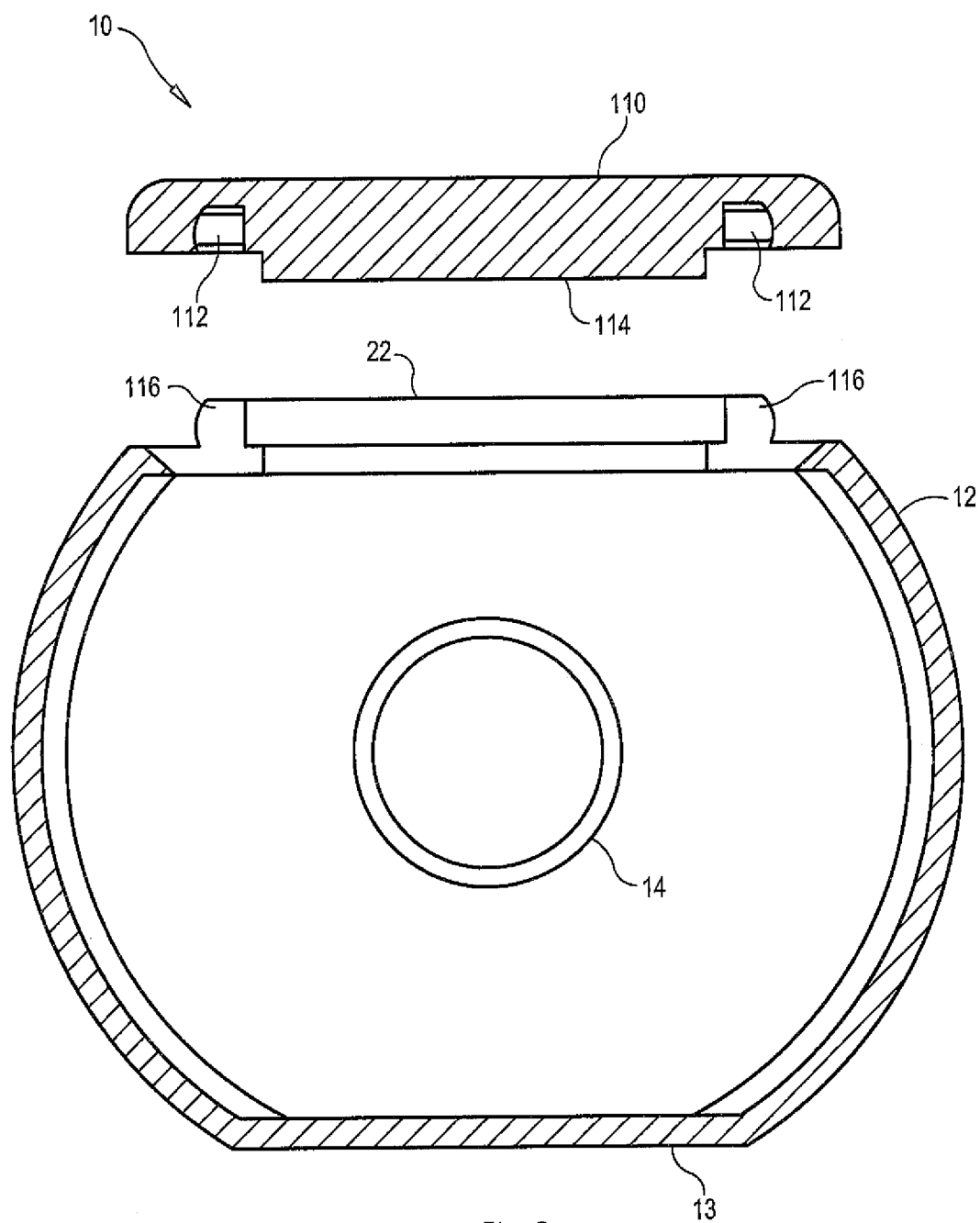
FIG. 9 is a cross sectional view of the quantitative sample transfer device and lid detached from the body segment showing the preferred structure for snapping the lid to the body segment in accordance with the instant invention.
Figure 35:
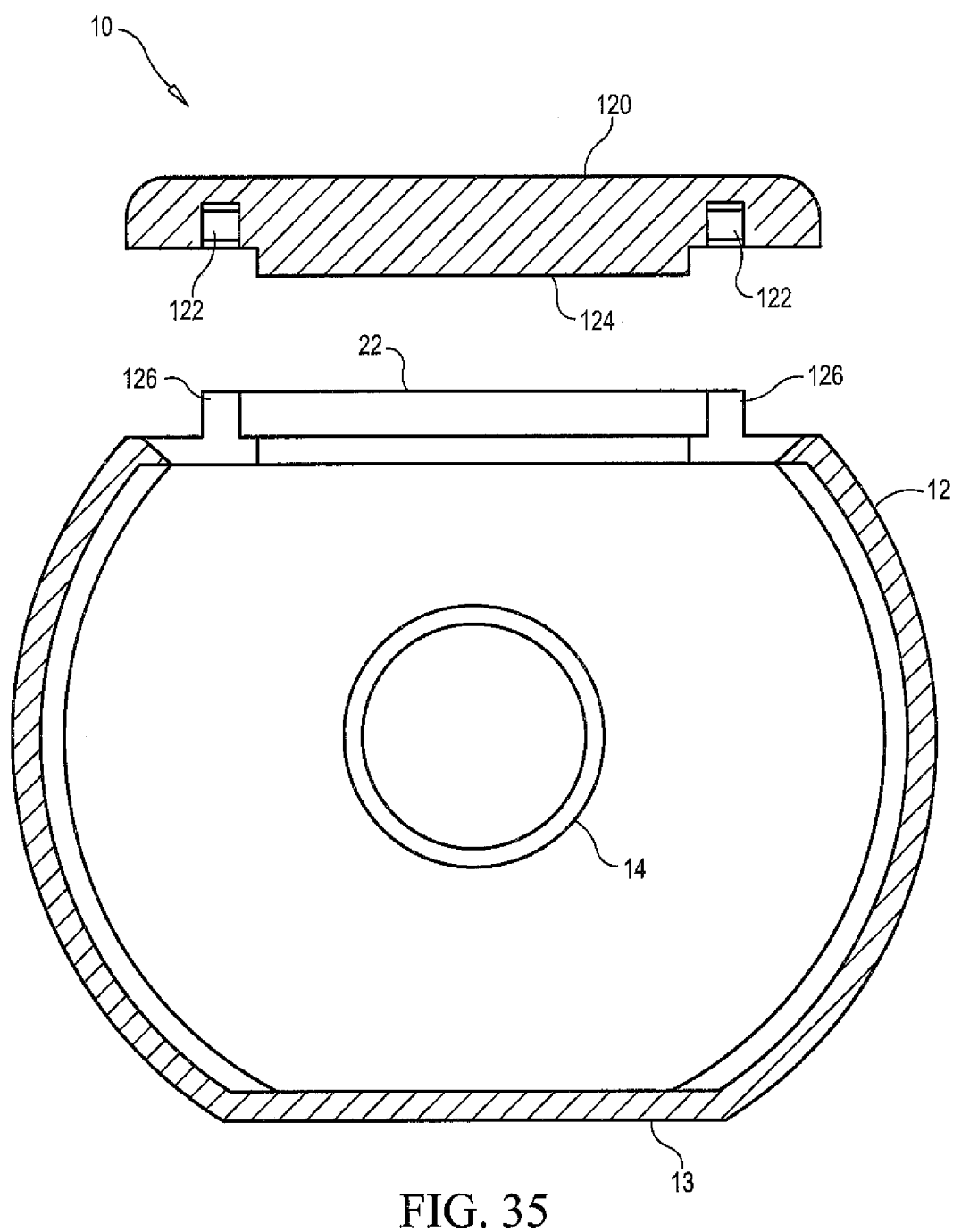
FIG. 35 is a cross sectional view of the quantitative sample transfer device and lid detached from the body segment showing a fourth structure for snapping the lid to the body segment in accordance with the instant invention.
Figure 36:
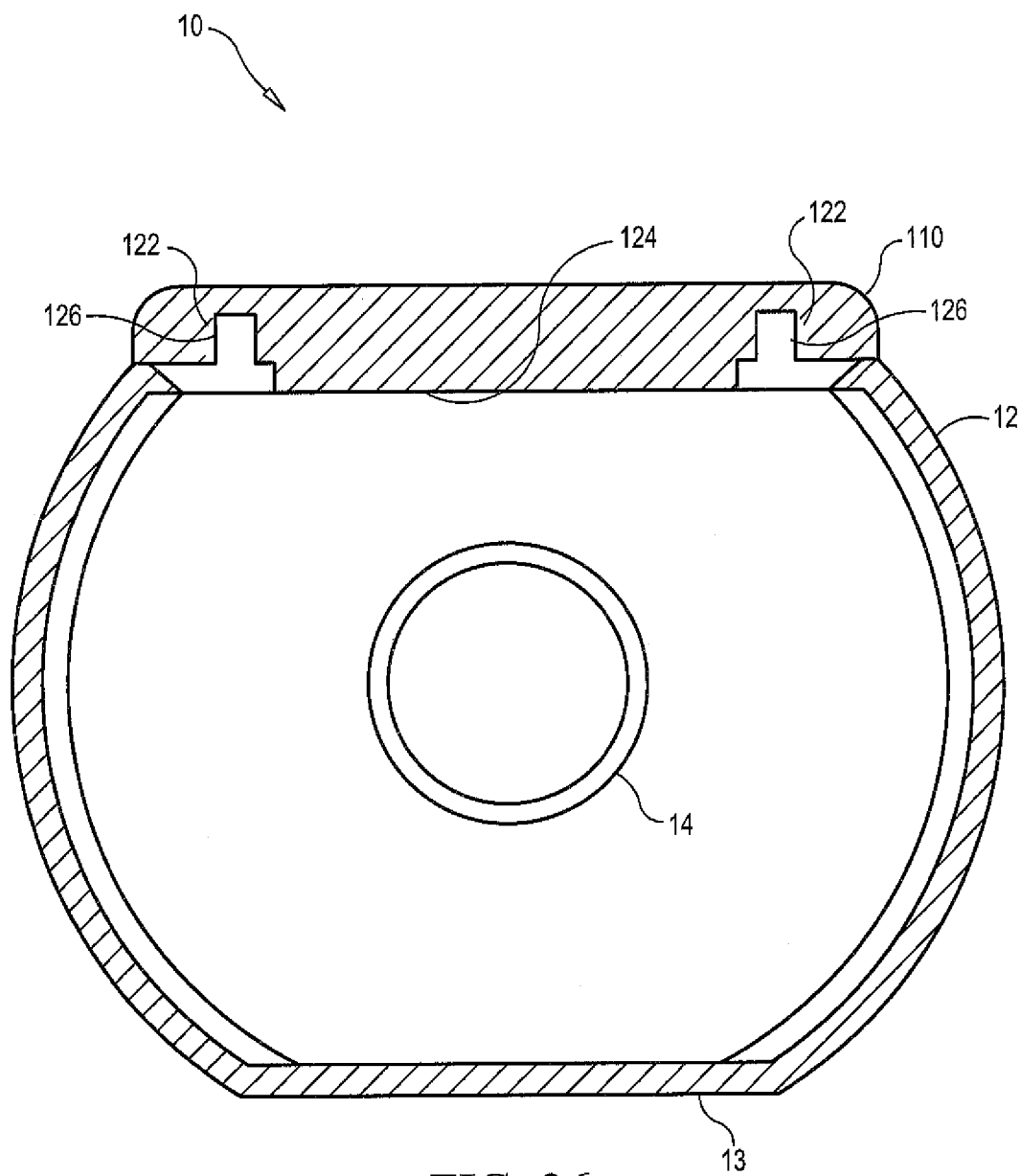
FIG. 36 is a cross sectional view of the quantitative sample transfer device with the lid attached to the body segment showing the fourth snapping structure in accordance with the instant invention.
Figure 37:
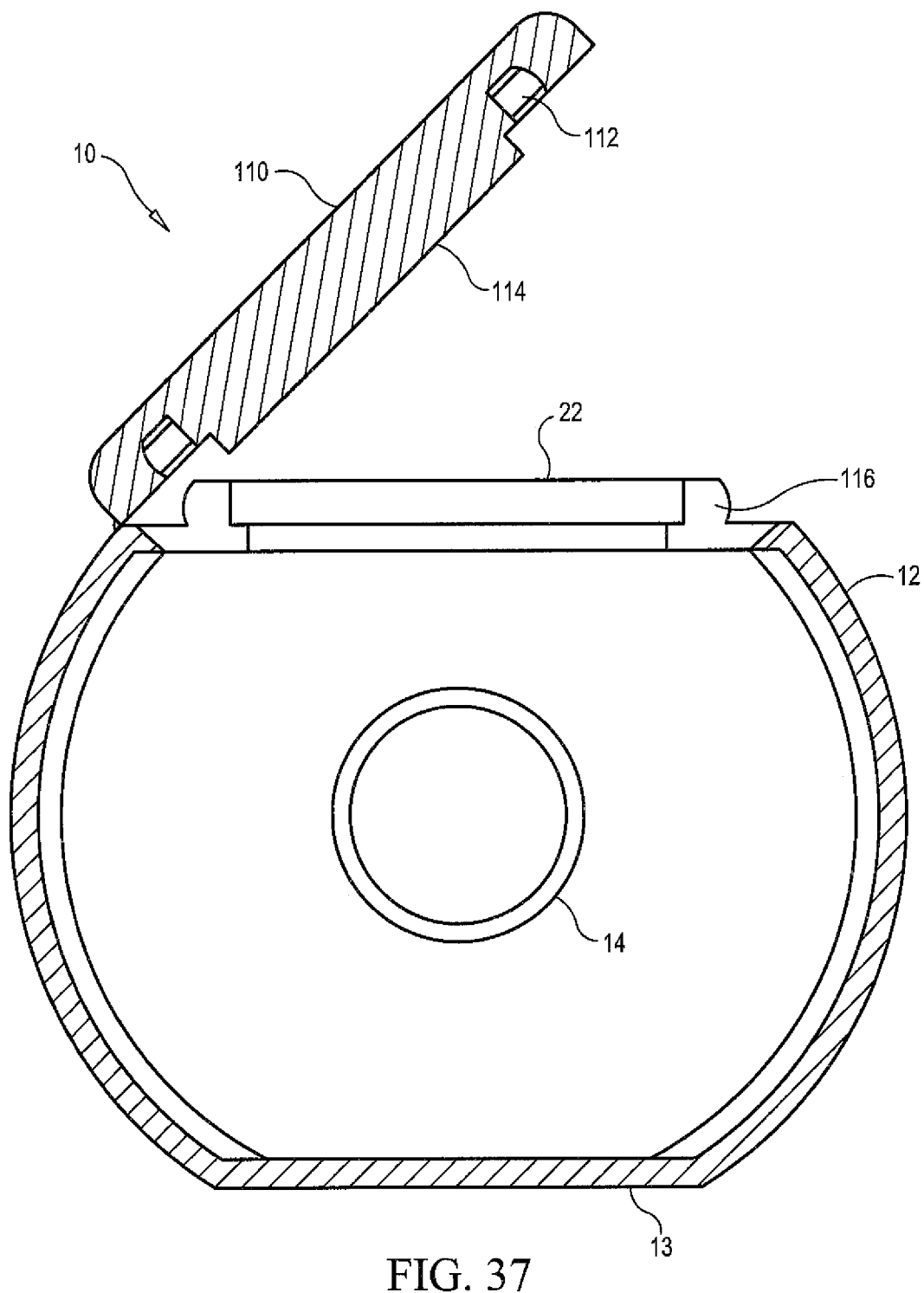
FIG. 37 is a cross sectional view of the quantitative sample transfer device and lid hinged to the body segment and opened showing a fifth structure for snapping the lid to the body segment in accordance with the instant invention.
Figure 38:
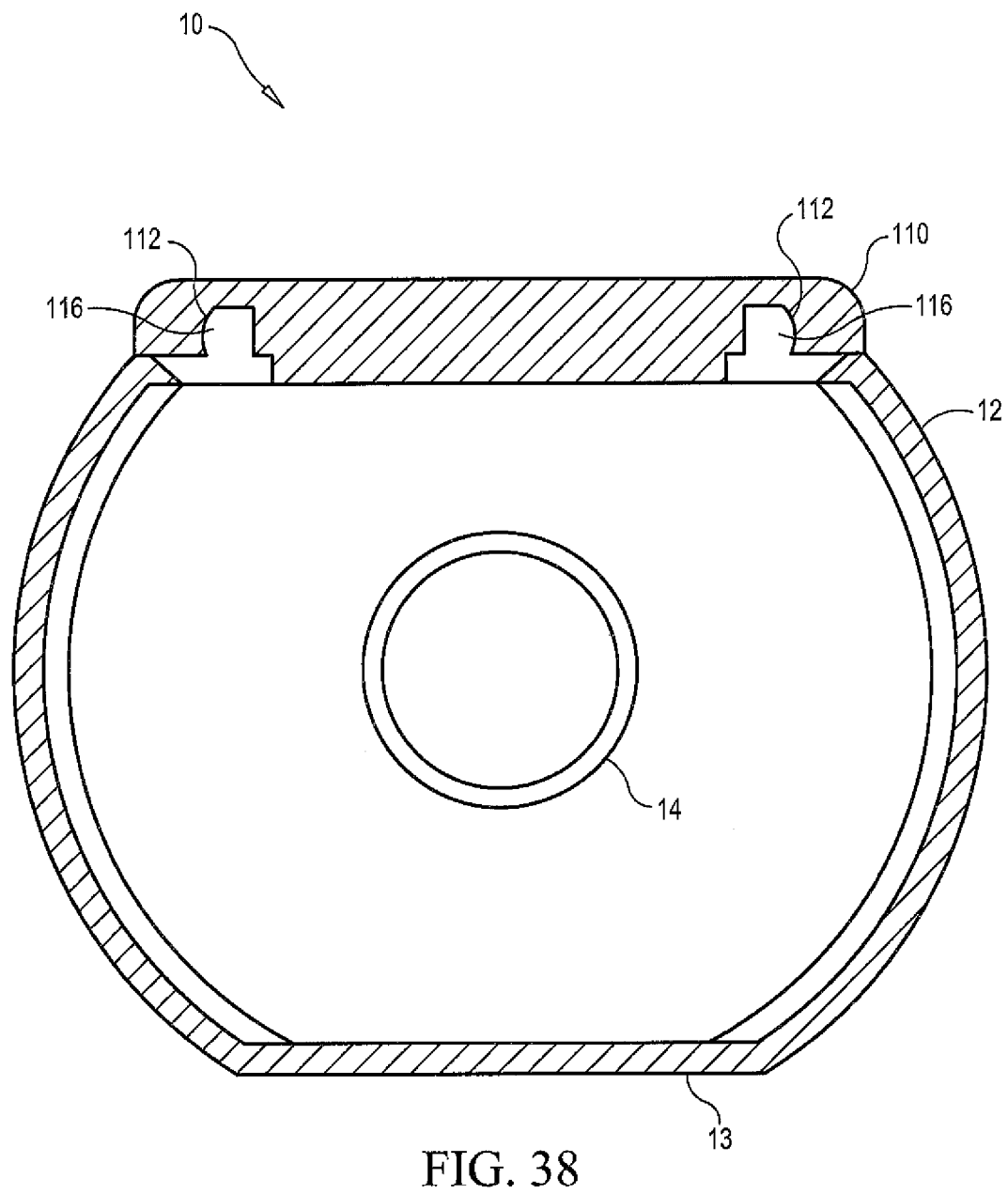
FIG. 38 is a cross sectional view of the quantitative sample transfer device and lid hinged to the body segment and closed showing the fifth structure for snapping the lid to the body segment in accordance with the instant invention.
Figure 39:
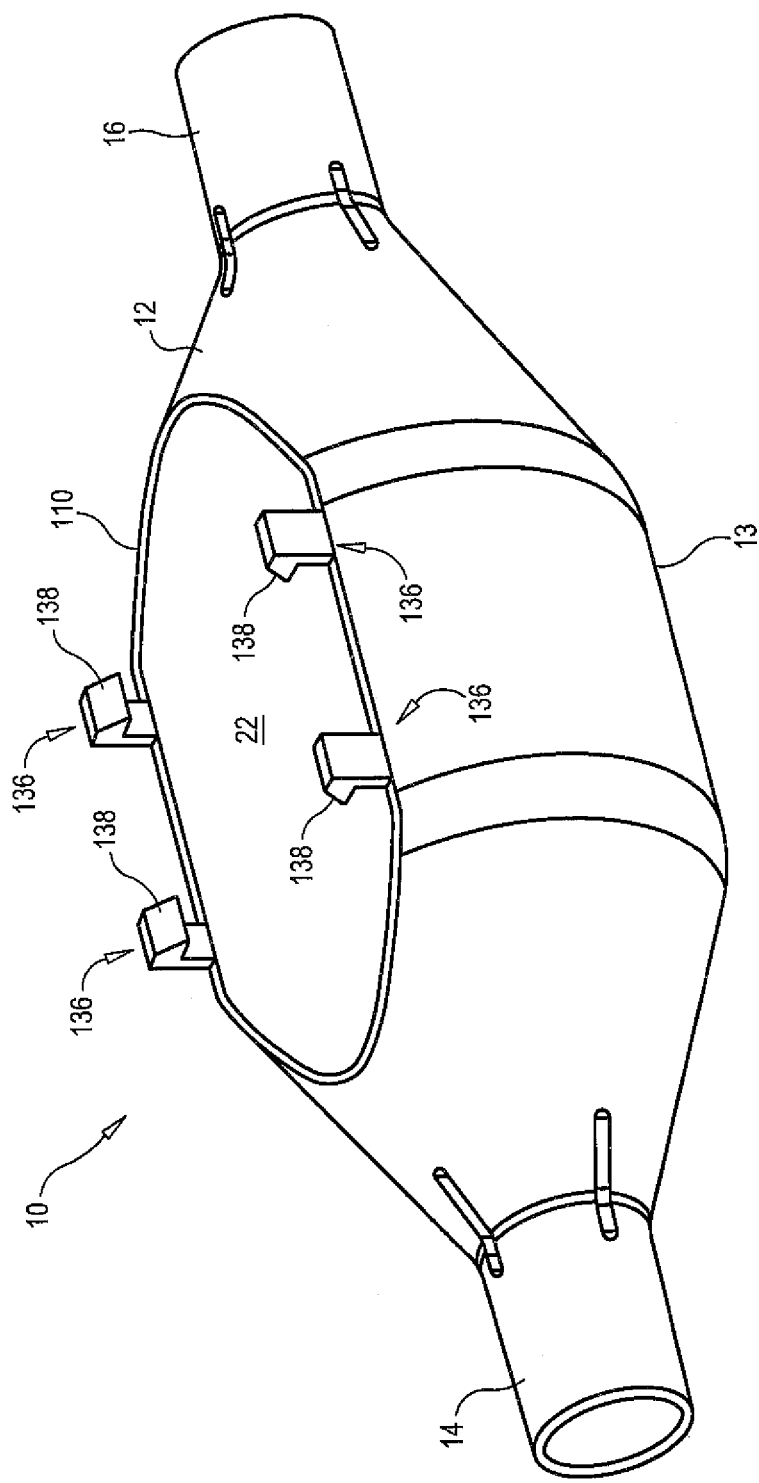
FIG. 39 is a perspective view of the body segment of the quantitative sample transfer device without a lid showing a sixth structure for snapping the lid to the body segment in accordance with the instant invention.
Figure 40:
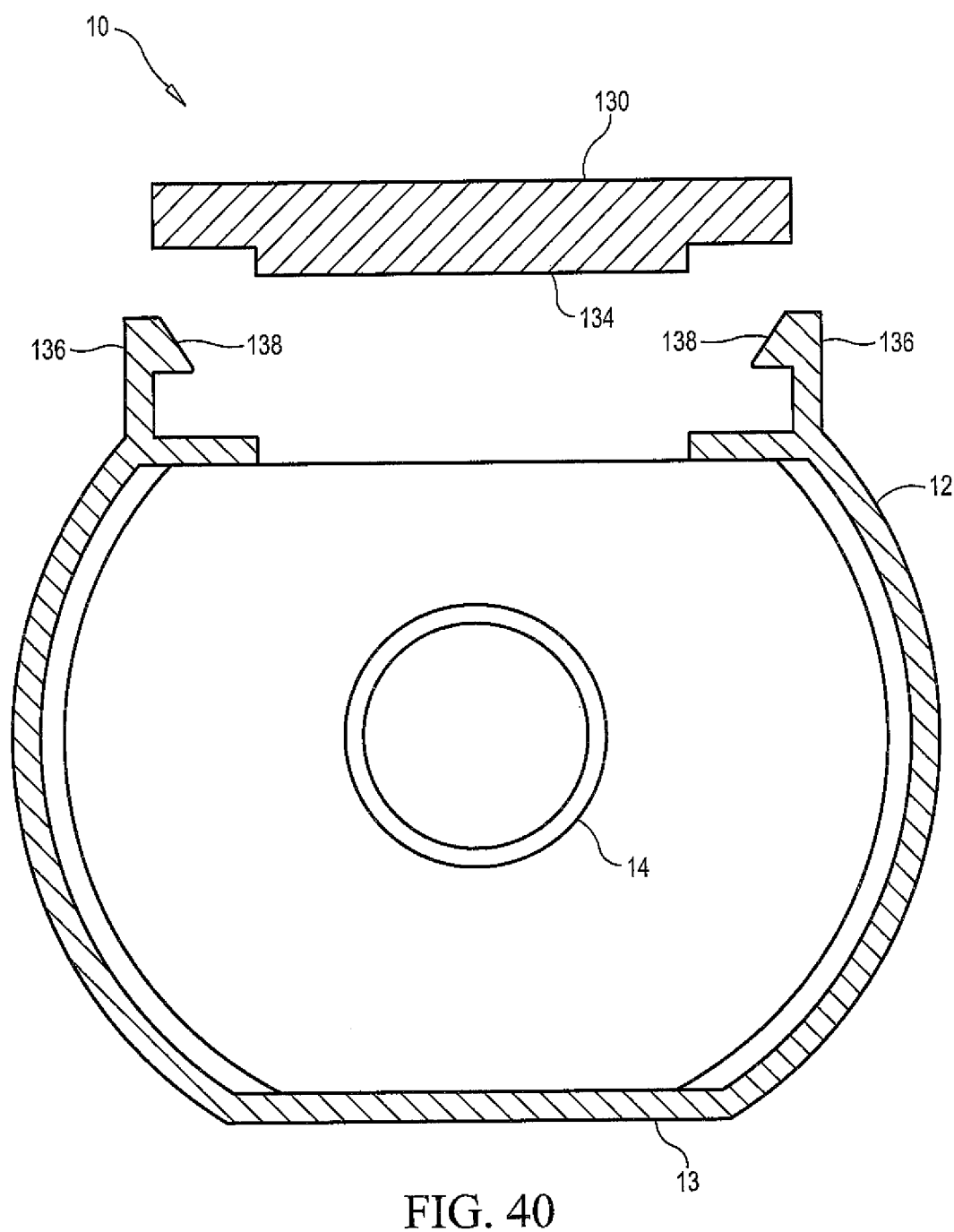
FIG. 40 is a cross sectional view of the sixth snapping structure of the quantitative sample transfer device without the lid attached to the body segment in accordance with the instant invention.
Figure 41:
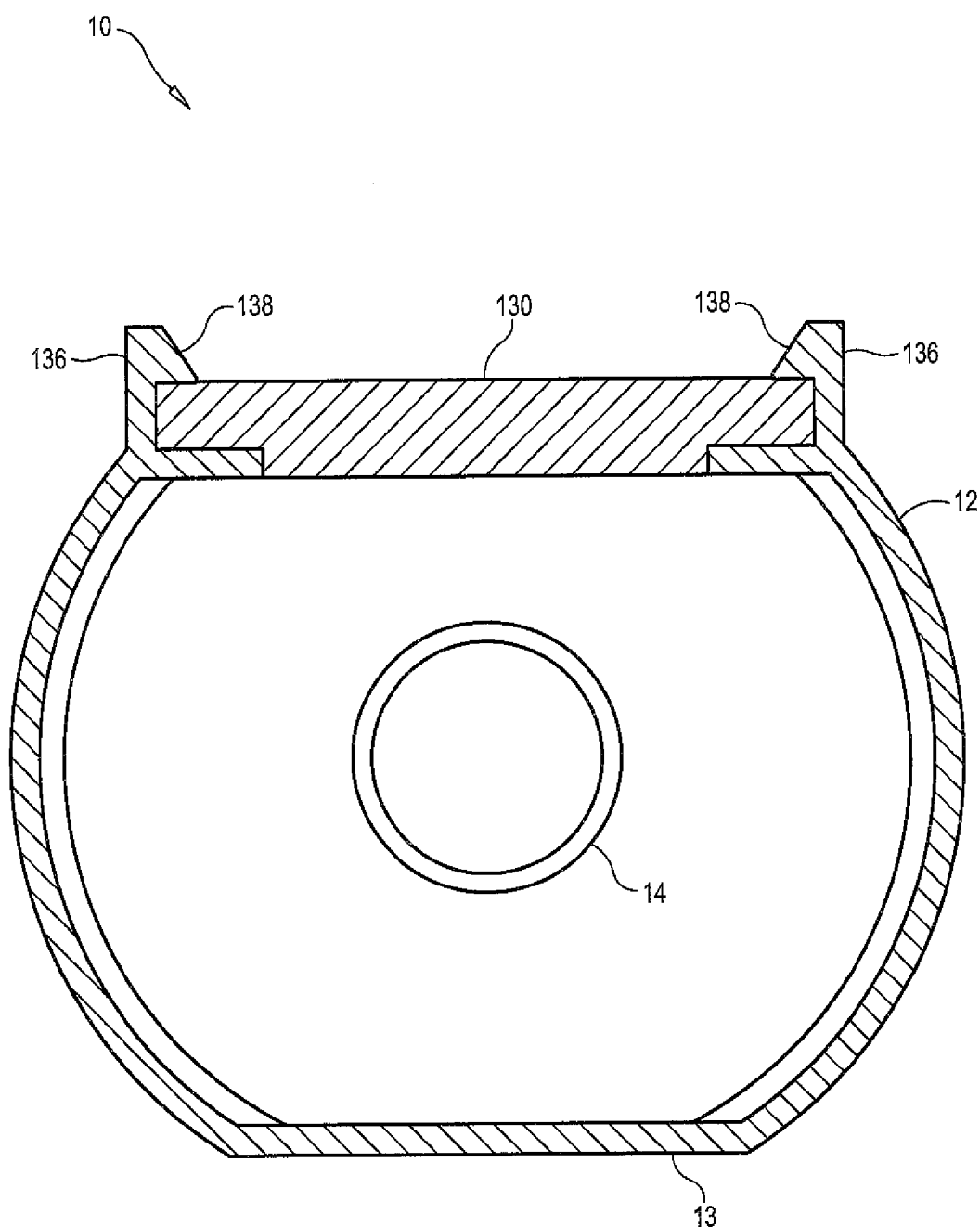
FIG. 41 is a cross sectional view of the seventh snapping structure of the quantitative sample transfer device with the lid attached to the body segment in accordance with the instant invention.

The instant invention 10 may comprise structure for snapping the lid to the body segment as shown in FIGS. 9-10 and 35-41. Referring to FIG. 9, in a fourth embodiment for snapping the lid to the body segment, the transfer device 10 comprises a central body segment 12 having a partially curved rail 116 projecting upward from and around the periphery of the body segment 12 and a lid 110 having a corresponding partially curved groove 112 formed around the periphery of the lid's lower periphery surface and a depending lip 114. The rail 116 has a flat inner surface and a curved outer surface. Likewise, the lid channel 112 has a corresponding curved surface and flat surface. When the lid 110 and body segment 12 are aligned and pressed together, the rail 116 snaps into the channel 112 and the lip 114 intersects the opening 22, as shown in FIG. 10. Referring to FIG. 35, in a fifth embodiment for snapping the lid to the body segment, the transfer device 10 comprises a central body segment 12 having a rail 126 projecting upward from and around the periphery of the body segment 12 and a lid 120 having a corresponding groove 122 formed around the periphery of the lid's lower periphery surface and a depending lip 124. When the lid 120 and body segment 12 are aligned and pressed together, the rail 116 snaps into the channel and, or the lip 124 intersects and snaps over the edge forming the opening 22, as shown in FIG. 36. Referring to FIG. 37, in the sixth embodiment for snapping the lid to the body segment comprises the snapping structure of the fourth embodiment wherein the lid 110 is hinged to the body segment. As in the fourth embodiment, in the sixth snapping embodiment, the transfer device 10 comprises the central body segment 12 having a partially curved rail 116 projecting upward from and around the periphery of the body segment 12 and a lid 110 having a corresponding partially curved groove 112 formed around the periphery of the lid's lower periphery surface and a depending lip 114. When the lid 110 is closed over the body segment 12, the rail 116 snaps into the channel 112 and the lip 114 intersects the opening 22. With reference to FIGS. 39-41, the seventh snapping embodiment comprises a body segment 12 having a pair of snapping levers 136 on each side of the opening for engaging the outer edge of a lid 130. The lid 130 comprises a depending lip 134 that intersects the opening 22 and a periphery edge that projects outward for resting on a shelf defined around the periphery of the opening 22.

The instant invention has been shown and described herein in what is considered to be the most practical and preferred embodiment. It is recognized, however, that departures may be made therefrom within the scope of the invention and that obvious structural and/or functional modifications will occur to a person skilled in the art.

What is claimed is:

1. A quantitative chemical, pharmaceutical, biological or environmental sample transfer device for weighing a sample and transferring it to a testing flask or container, said device comprising:
    a hollow body segment having an opening for receiving a sample to be weighed and tested;
    a first hollow neck defined at one end of said hollow body, said first neck having an opening, said first neck opening providing access to said hollow body through said first neck, said first neck being insertable into a testing flask,
    a second hollow neck defined at an opposite end of said hollow body, said second neck having an opening, said second neck opening providing access to said hollow body through said second neck, said second neck being insertable into a testing flask;
    a first removable cap adapted for mating with said first neck, said first removable cap occluding said first neck opening when mated with said first neck;
    a second removable cap adapted for mating with said second neck, said second removable cap occluding said second neck opening when mated with said second neck;
    a handleless lid adapted for covering said body segment opening, said lid defining a smooth continuous periphery edge devoid of a gripping portion; and
    means for unreleasably snapping said lid to said body segment over said body segment opening so as to seal said opening wherein said lid interlocks with said body such that said lid resist pulling forces and forms a substantially smooth seam devoid of raised ridges to virtually prevent being unsnapped from said body segment.

2. A device as recited in claim 1, wherein said first cap comprises:
    an extension portion that plugs into said first hollow neck opening.

3. A device as recited in claim 2, wherein said first cap comprises:
    a head portion, said extension portion projecting out from said head portion, said head portion having a wider cross section than said extension portion.

4. A device as recited in claim 2, wherein said second cap comprises:
    an extension portion that plugs into said second hollow neck opening.

5. A device as recited in claim 4, wherein said second cap comprises:
    a head portion, said extension portion projecting out from said head portion, said head portion having a wider cross section than said extension portion.

6. A device as recited in claim 4, wherein said first neck and said second neck have a smaller cross section than said hollow body segment.

7. A device as recited in claim 2, wherein said first hollow neck and said second hollow neck have a smaller cross section than said hollow body segment.

8. A device as recited in claim 1, wherein said first cap comprises:
    an extension portion that mounts over said first hollow neck opening.

9. A device as recited in claim 8, wherein said first cap comprises:
    a head portion, said extension portion projecting out from said head portion, said head portion having a wider cross section than said extension portion.

10. A device as recited in claim 8, wherein said first hollow neck and said second hollow neck have a smaller cross section than said hollow body segment.

11. A device as recited in claim 8, wherein said second cap comprises:
    an extension portion that mounts over said second neck opening.

12. A device as recited in claim 11, wherein said second cap comprises:
    a head portion, said extension portion projecting out from said head portion, said head portion having a wider cross section than said extension portion.

13. A device as recited in claim 11, wherein said first neck and said second neck have a smaller cross section than said hollow body segment.

14. A device as recited in claim 1, wherein said device further comprises:

at least one ridge projecting outward from an outer surface of said first hollow neck, said ridge and said first neck defining a vent when said first neck is inserted into a testing flask.

15. A device as recited in claim 1, wherein said device further comprises:
   a flared opening defined by said first hollow neck or said second hollow neck.

16. A device as recited in claim 1, wherein said body segment comprises:
   a first body segment; and
   a second body segment, said first and second body segments being permanently attachable together.

17. A device as recited in claim 16, wherein said first body segment is hinged to said second body segment.

18. A device as recited in claim 1, wherein said lid is hinged to said body segment.

19. A device as recited in claim 1, wherein said means for unreleasably snapping said lid to said body segment comprises:
   a rail projecting upward from and around a periphery of said body segment; and
   a corresponding channel formed around the periphery of and in said lid wherein said rail and said channel are adapted for snapping together, a smooth transition seam defined between said lid and said body segment when said lid is snapped to said body segment such that said lid is resistant to being unsnapped from said body segment.

20. A device as recited in claim 19, wherein said means for unreleasably snapping said lid to said body segment comprises:
   a lip depending from said lid adjacent said channel, said lip intersecting said body segment opening when said lid is mounted to said body segment over said body segment opening.

\* \* \* \* \*